US00RE42526E

(19) United States
(12) Reissued Patent
Reiser et al.

(10) Patent Number: US RE42,526 E
(45) Date of Reissued Patent: Jul. 5, 2011

(54) BICORTICAL TIBIAL FIXATION OF ACL GRAFTS

(75) Inventors: Bernard Reiser, Pfinztal (DE); Reinhold Schmieding, Naples, FL (US)

(73) Assignee: Arthrex, Inc., Naples, FL (US)

(21) Appl. No.: 10/365,628

(22) Filed: Jun. 12, 2003

Related U.S. Patent Documents

Reissue of:
(64) Patent No.: 6,387,129
Issued: May 14, 2002
Appl. No.: 09/259,302
Filed: Mar. 1, 1999

U.S. Applications:
(63) Continuation-in-part of application No. 09/243,995, filed on Feb. 4, 1999, now abandoned.

(60) Provisional application No. 60/078,391, filed on Mar. 18, 1998.

(51) Int. Cl.
*A61F 2/08* (2006.01)

(52) U.S. Cl. ..... 623/13.14

(58) Field of Classification Search ..... 623/13.12, 623/13.14, 13.11–13.2; 606/99, 326, 308, 606/321, 310, 305
See application file for complete search history.

(56) References Cited

U.S. PATENT DOCUMENTS

| | | | | | |
|---|---|---|---|---|---|
| 3,953,896 | A | * | 5/1976 | Treace | 623/13.12 |
| 4,301,551 | A | * | 11/1981 | Dore et al. | 623/13.13 |
| 4,456,005 | A | * | 6/1984 | Lichty | 606/60 |
| 4,463,753 | A | * | 8/1984 | Gustilo | 606/308 |
| 4,605,414 | A | | 8/1986 | Czajka | |
| 4,744,793 | A | * | 5/1988 | Parr et al. | 623/13.14 |
| 4,755,183 | A | * | 7/1988 | Kenna | 623/13.14 |
| 4,772,286 | A | * | 9/1988 | Goble et al. | 623/13.14 |
| 4,828,562 | A | * | 5/1989 | Kenna | 623/13.13 |
| 4,870,957 | A | * | 10/1989 | Goble et al. | 623/13.12 |
| 4,927,421 | A | * | 5/1990 | Goble et al. | 606/232 |
| 5,004,474 | A | * | 4/1991 | Fronk et al. | 623/13.14 |
| 5,062,843 | A | * | 11/1991 | Mahony, III | 606/73 |
| 5,108,433 | A | * | 4/1992 | May et al. | 623/13 |
| 5,116,337 | A | | 5/1992 | Johnson | |
| 5,151,104 | A | * | 9/1992 | Kenna | 606/73 |
| 5,211,647 | A | * | 5/1993 | Schmieding | 606/104 |
| 5,234,430 | A | * | 8/1993 | Huebner | 606/60 |

(Continued)

OTHER PUBLICATIONS

"Orthopedic Screw Machined in One Step", Tooling and Production, Apr. 1994.

(Continued)

*Primary Examiner* — Alvin J. Stewart
(74) *Attorney, Agent, or Firm* — Dickstein Shapiro LLP

(57) ABSTRACT

A method of securing a graft in a bone tunnel, in which graft is secured within the tunnel at both the entrance and the exit ends of the tunnel to provide bicortical fixation of the graft in the bone. Interference screws or other fixation devices are used to secure the graft within the tunnel. For tibial tunnel fixation using an interference screw, the back end of the distal screw is angled so that it closely approximates the angle of the outer tibial tunnel rim. The distal screw is non-cannulated to prevent hematomas from being formed by blood flowing from the tibial tunnel into the surrounding soft tissue. The proximal screw has a restricted cannula to minimize the flow of synovial fluid entering the tibial tunnel. Advantageously, the space between the two screws fills with blood to promote faster healing and incorporation of the graft in the tibial tunnel.

13 Claims, 5 Drawing Sheets

U.S. PATENT DOCUMENTS 5,282,802 A * 2/1994 Mahony, III ..... 606/72
5,364,400 A * 11/1994 Rego et al. ..... 606/304
5,370,662 A * 12/1994 Stone et al. ..... 606/232
RE34,871 E * 3/1995 McGuire et al. ..... 623/13.13
5,397,357 A * 3/1995 Schmieding et al. ..... 606/86 R
5,423,819 A 6/1995 Small et al.
5,456,685 A 10/1995 Huebner
5,470,334 A * 11/1995 Ross et al. ..... 606/72
5,496,326 A 3/1996 Johnson
5,505,731 A * 4/1996 Tornier ..... 606/261
5,507,812 A * 4/1996 Moore ..... 623/13.13
5,562,669 A * 10/1996 McGuire ..... 623/13.12
5,562,671 A * 10/1996 Globe et al. ..... 606/73
5,632,748 A 5/1997 Beck, Jr. et al.
5,871,504 A 2/1999 Eaton et al.
5,895,425 A * 4/1999 Grafton et al. ..... 606/304
5,899,938 A * 5/1999 Sklar et al. ..... 623/13.14
5,925,048 A * 7/1999 Ahmad et al. ..... 606/308
5,957,924 A * 9/1999 Tormala et al. ..... 606/72
5,961,520 A * 10/1999 Beck et al. ..... 606/72
5,968,045 A * 10/1999 Frazier ..... 606/304
5,993,486 A * 11/1999 Tomatsu ..... 623/13.11
6,001,101 A * 12/1999 Augagneur et al. ..... 606/316
6,019,759 A * 2/2000 Rogozinski ..... 606/308
6,099,568 A * 8/2000 Simonian et al. ..... 623/13.11
6,123,710 A * 9/2000 Pinczewski et al. ..... 606/73
6,221,107 B1 * 4/2001 Steiner et al. ..... 623/13.14
6,235,057 B1 * 5/2001 Roger et al. ..... 623/13.12
6,264,694 B1 * 7/2001 Weiler ..... 623/13.14
6,616,694 B1 * 9/2003 Hart ..... 623/13.14
6,629,977 B1 * 10/2003 Wolf ..... 606/73
6,953,463 B2 * 10/2005 West, Jr. ..... 606/73
7,083,647 B1 * 8/2006 Sklar et al. ..... 623/13.14
7,235,078 B2 * 6/2007 West, Jr. ..... 606/916

OTHER PUBLICATIONS

Mark H. Gonzalez, M.D. and Robert F. Hall, Jr. "Intramedullary Fixation of Metacarpal and Proximal Phalangeal Fractures of the Hand", pp. 47-54, Clinical Orthopaedics and Related Research, No. 327, 1996.

Thomas A. Russell, et al. "Mechanical Characterization of Femoral Interlocking Intramedullary Nailing Systems", pp. 332-340, Journal of Orthopaedic Trauma, Vol. 5, No. 3, 1991.

* cited by examiner

BICORTICAL TIBIAL FIXATION OF ACL GRAFTS

Matter enclosed in heavy brackets [ ] appears in the original patent but forms no part of this reissue specification; matter printed in italics indicates the additions made by reissue.

This application claims the benefit of U.S. Provisional Application Ser. No. 60/078,391, filed Mar. 18, 1998, and is a continuation-in-part of U.S. patent application Ser. No. 09/243,995, filed Feb. 4, 1999, now abandoned, the disclosures of which are incorporated herein by reference.

BACKGROUND OF THE INVENTION

1. Field of the Invention

The present invention relates to endosteal fixation of a ligament by device insertion and, more specifically, to methods and devices for bicortical tibial fixation of anterior cruciate ligament grafts.

2. Description of the Related Art

When a ligament becomes detached from a bone, surgery usually is required to reconstruct the ligament. Often, a substitute ligament or graft is secured into bone tunnels to facilitate incorporation and permanent attachment.

Various methods of graft attachment are known, including the use of interference screws to secure the graft against the walls of a tunnel drilled through the tibia and a socket formed in the femur. A strong graft attachment is obtained by using a metal interference screw to wedge a graft bone block to the wall of a graft tunnel formed through the bone, as disclosed in U.S. Pat. No. 5,211,647 to Schmieding. If a bioabsorbable interference screw is used, the graft can be wedged directly against the bone by the screw, without a bone component.

In either case, the graft usually is secured as close as possible to the normal ligament origin and insertion site, which are at the top of the tibial tunnel (the tibial plateau) and the entrance to the femoral socket in ACL reconstructions. The portion of the graft extending out the bottom of the tibia is ordinarily secured to the outside of the bone with a staple or using screw/washer fixation.

The above-described secondary fixation of the graft to the exterior surface of the tibia is disadvantageous in that it is subject to abrasion from external elements, and is generally less secure than internal fixation. Accordingly, a graft fixation technique is needed which provides increased fixation strength of the graft in the tibial tunnel, and improved healing of the tibial tunnel and associated tissue.

SUMMARY OF THE INVENTION

The present invention overcomes the disadvantages of the prior art and achieves the foregoing objectives by providing apparatus and methods for bicortical fixation of ligament grafts, whereby the graft is fixed at two cortical locations ("bicortical") within the tibial tunnel using a pair of fixation devices. The invention advantageously improves fixation strength, and also minimizes the likelihood of damage to the graft and the bone tunnel during and after fixation, such as by preventing widening of the bone tunnel by graft motion. In addition, as described below, bicortical fixation improves the healing environment of the ligament graft.

The fixation strength of the graft is advantageously increased by engaging the graft against the denser, cortical bone at the ends of the tunnel. The fixation method and devices of the present invention preferably are designed to match the anatomy of the tibial tunnel, and to provide fixation at the original insertion point of the ligament. The fixation devices also are designed to minimize graft abrasion, while maximizing fixation strength.

Further, the preferred fixation methods and devices advantageously restrict blood loss from the fixation site to improve healing and graft incorporation. The preferred fixation modes advantageously plug both ends of the bone tunnel, and leave the internal bone tunnel cavity unobstructed between the plugged ends. Accordingly, the bone tunnel cavity, through which the graft passes, is allowed to fill with serous fluids to promote faster healing and enhance graft incorporation within the tunnel.

Various modes of fixation can be used in the present invention, including, for example, interference screws, wedges, expanding devices, and adhesives. Preferred alterative devices are those that securely engage the cortical wall of the tunnel, and preferably include threads, ridges, and/or other enhancements to maximize bone fixation.

Preferred methods and devices disclosed herein utilize interference screw fixation, although any other type of fixation device capable of being secured bicortically also could be used. Further, identical modes of fixation need not be used at both ends of the tunnel. Preferably, the mode of fixation also will at least substantially occlude both ends of the bone tunnel, resulting in the further advantage of an improved healing environment within the tunnel, as described further below.

According to a preferred embodiment using interference screw fixation, the interference screws used in the present invention preferably have a hex socket for receiving a hex-head screwdriver. The hex socket extends substantially the length of the screw to optimize the distribution of insertion torque along the length of the screws. In order to maintain wall thickness, the hex socket is tapered in correspondence with the tapered outer profile of the device. The taper also permits easy insertion of the hex driver (also tapered) into the fixation screw. A cannulated hex-head screwdriver is used for guide pin insertion methods.

The interference screws preferably are fully-threaded to maximize fixation strength within the tunnel. Preferably, the proximal screw (i.e., the screw closest to the joint) has a smooth, rounded tip profile so as to minimize abrasion with the graft. The distal screw (i.e., the screw farthest from the joint) has an angled back end so that it can be oriented substantially flush with the outer surface of the bone (e.g., the tibia) into which the screw has been installed. These and other features for minimizing graft abrasion and maximizing graft fixation also apply to the other modes of bicortical fixation envisioned by the present invention.

The fixation devices of the present invention, preferably interference screws, optimally are formed of a bioabsorbable material. Bioabsorbable materials known to those of skill in the art include poly-(L-lactic acid) (PLA), poly-(D,L-lactide), and poly glycolic acid (PGA), for example. Other bioabsorbable, non-metallic materials, especially those tailored for hardness, tensile strength, and compressive strength may be utilized. Other known biocompatible materials which could be used include plastics, titanium, titanium alloys, allograft bone, and inert bone substitute materials.

In the preferred method of ACL reconstruction of the present invention, the graft (preferably a hamstring tendon autograft or allograft) is secured femorally preferably by interference screw fixation in a socket formed through the tibial tunnel, as described, for example, in U.S. Pat. No. 5,320,626, the disclosure of which is incorporated herein by reference. The preferred femoral interference screw is inserted into the femoral socket, and has a rounded back end to prevent tissue damage after insertion. Other forms of femoral fixation also could be used.

Bicortical tibial fixation is provided by delivering the proximal fixation device to the inner opening of the tibial tunnel and installing the device to secure the ligament graft at the anatomical position on the tibial plateau. The distal device is delivered and installed to secure the graft within the tibial tunnel at the outer end of the tunnel. Prior to device insertion, the tunnel may be pre-tapped and/or dilated to enhance interference fixation.

A guide pin preferably is employed as necessary to guide the femoral interference screw and the proximal tibial interference screw during delivery and installation. For this reason, these two devices preferably are fully cannulated. The distal tibial screw, on the other hand, preferably is non-cannulated, to prevent blood from flowing from the tibial tunnel and into the surrounding tissue.

Femoral graft insertion and fixation can be achieved by various methods and devices known in the art, including the transverse, intraosseous pin and technique disclosed in allowed U.S. patent application Ser. No. 09/015,618, filed Jan. 29, 1998, or in U.S. Pat. No. 5,601,562, the disclosures of which are incorporated herein by reference.

Other features and advantages of the present invention will become apparent from the following description of the invention which refers to the accompanying drawings.

DETAILED DESCRIPTION OF THE PREFERRED EMBODIMENTS

Figure 1:
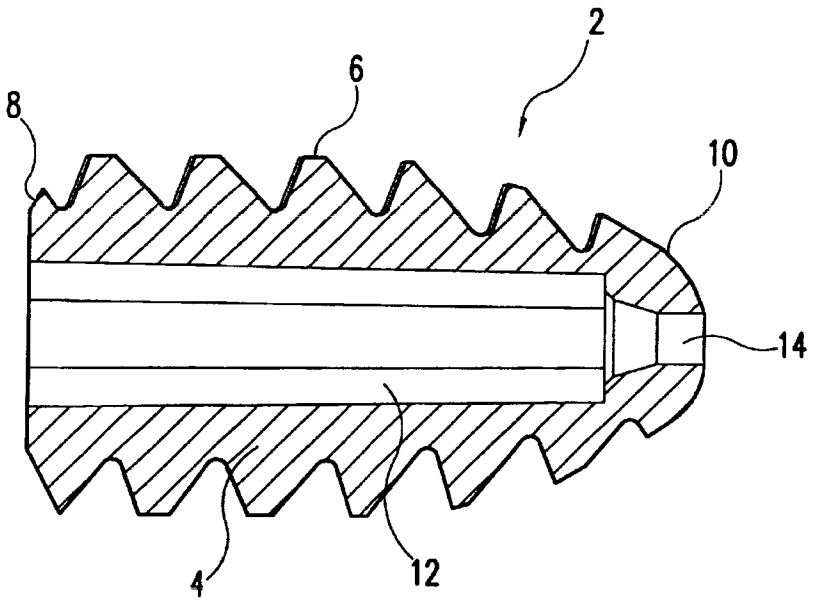
FIG. 1 is a cut-away plan view of a proximal tibial interference screw according to the present invention.
Figure 2:
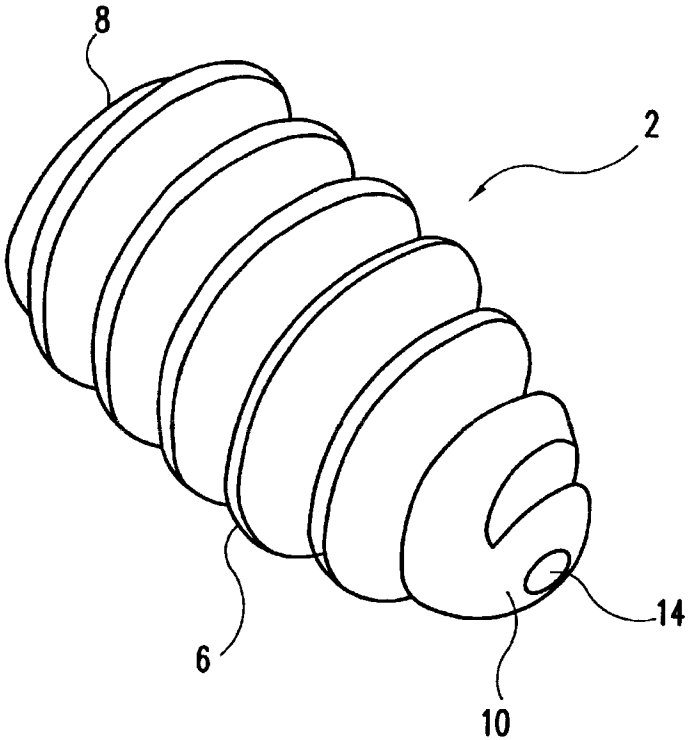
FIG. 2 is a perspective view of the proximal tibial interference screw of FIG. 1.

Referring to FIGS. 1 and 2, a proximal interference screw 2 for fixation of an ACL graft according to the present invention is shown. The screw fixates the graft in the tibial tunnel, and is installed at the normal ligament anatomical insertion at the tibial plateau according to a preferred method described more fully below. Proximal screw 2 includes a body 4 around which a continuous thread 6 is formed. Thread 6 extends to the back end 8 of the screw 2. The front end 10 of screw 2 has a rounded profile. Thread 6 terminates somewhat away from the front end 10.

Screw 2 has a hexagonal socket 12 which tapers inwardly and extends from the back end substantially to the front end of the screw. At front end 10, a small, circular cannula 14 is formed for receiving a guide wire or pin. The smaller opening minimizes the amount of synovial fluid which can flow through the screw from the joint space into the interbone space of the tibial tunnel; synovial fluid can retard sharpie fiber growth into the graft within the bone tunnel.

Figure 3:
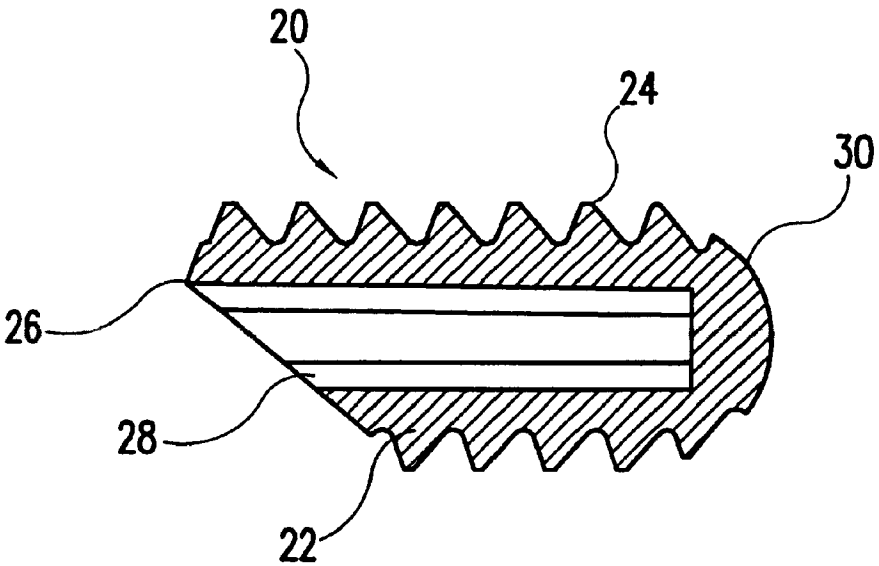
FIG. 3 is a cut-away plan view of a distal tibial interference screw according to the present invention taken along the line III—III in FIG. 4.
Figure 4:
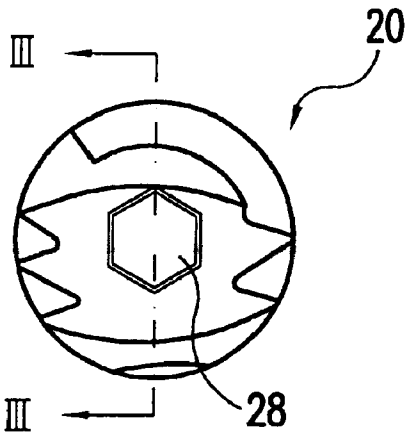
FIG. 4 is a back end view of the distal tibial interference screw of FIG. 3.

Referring to FIGS. 3 and 4, a distal tibial interference screw 20 having an angled back end is shown. Distal tibial interference screw 20 includes a body 22 around which a substantially continuous thread 24 is formed. The back end 26 of the screw is formed with an angled profile which, upon insertion, is aligned by rotation with the adjacent tibial bone surface to prevent damage to nearby tissue while maximizing fixation in the angled tibial tunnel. The front end 28 of screw 20 is tapered.

Distal interference screw 20 has a hexagonal socket 28 which tapers inwardly and extends from the back end substantially to the front end of the screw. Front end 30 is not cannulated. Accordingly, the screw advantageously plugs the distal end of the tibial tunnel to prevent blood from flowing into the surrounding soft tissue.

Figure 5:
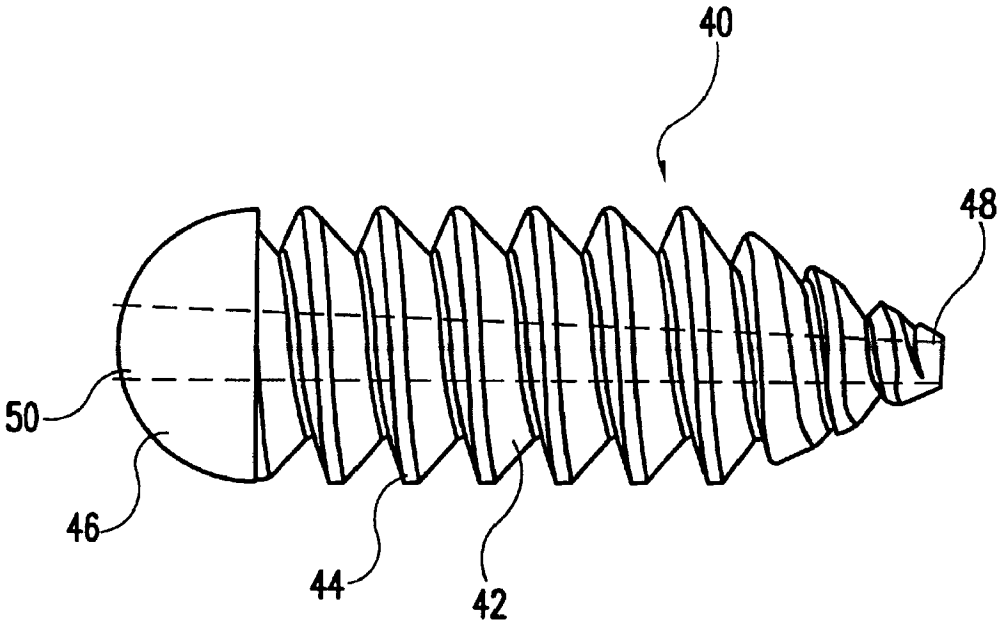
FIG. 5 is a plan view of a femoral interference screw according to the present invention.
Figure 6:
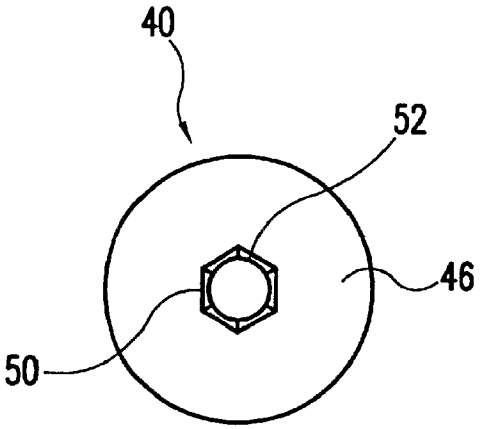
FIG. 6 is a back end view of the femoral interference screw of FIG. 5.

Referring to FIGS. 5 and 6, a femoral interference screw 40 having a rounded back end or head is shown. Femoral interference screw 40 includes a body 42 around which a continuous thread 44 is formed. Thread 44 terminates before reaching the back end 46 of the screw 40, the back end being formed with a hemispherical, smooth rounded profile.

Screw 40 has a tapered front end 48 terminating in a flat profile. Thread 44 extends substantially to the tip of the screw. Screw 40 is fully cannulated with a hexagonal socket 50 which tapers inwardly from the back end to the front end of the screw. At front end 48, the socket is formed to provide a substantially circular edge 52.

Figure 7:
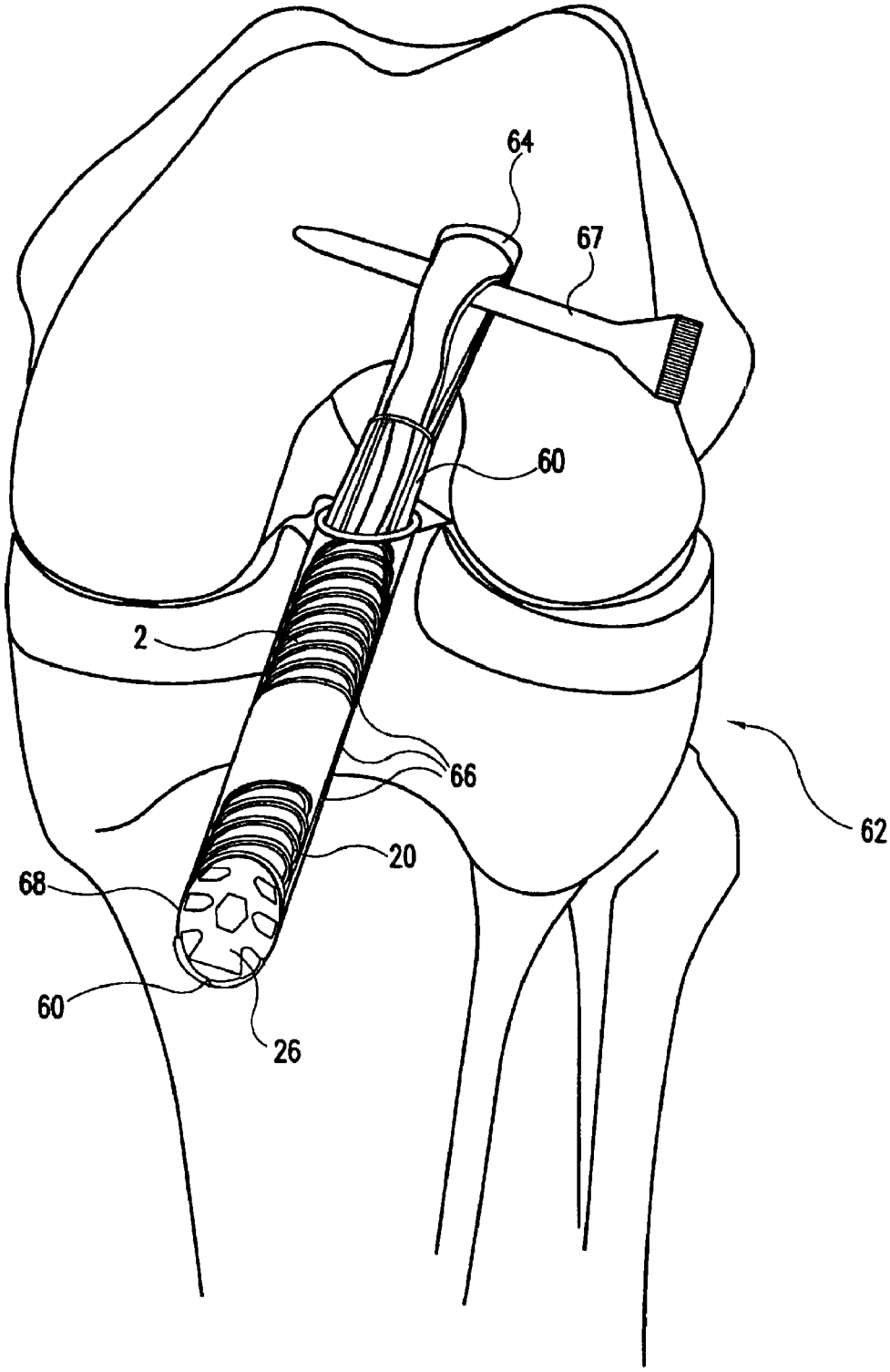
FIG. 7 shows schematically the completed steps in a preferred method of securing a graft in a graft tunnel according to the present invention.

Referring to FIG. 7, a graft 60 is shown having been inserted into a knee 62 inside of a femoral socket 64 and a tibial tunnel 66.

In the method of the present invention, once the graft has been accurately sized, a tunnel is created with a combination of drilling and/or cancellous bone dilation. The tibial tunnel angles proximally from the anterior portion of the tibia to the tibial plateau at an angle of approximately 50°. The tunnel preferably is about 50 mm in length. The tunnel preferably is drilled initially 1 or 2 mm smaller than the final diameter depending on the density of the bone. Subsequent dilation of the tunnel increases the level of fixation and insertion torque especially in the tibia where the cancellous bone is less dense. Preferably, the socket is formed by first drilling the tibial tunnel and then inserting a drill through the tibial tunnel and boring into the femur using a guide such as the guide disclosed in U.S. Pat. No. 5,320,626, the disclosure of which is incorporated herein by reference.

In the method of the present invention, graft 60 is first inserted into femoral socket 64. Before securing the graft into the femur, sutures on the graft preferably are tensioned on both ends while keeping the graft in position high in the femur. This dual tensioning helps prevent the graft from rotating during screw insertion. Transverse femoral pin 67 is then inserted through an arthroscopy portal to secure the graft in the femoral socket in accordance with the teachings of allowed application Ser. No. 09/015,618, previously incorporated by reference. Alternative methods include interference fixation using femoral interference screw 40 (FIGS. 5 and 6).

When employing femoral interference fixation, a femoral interference screw 40 is chosen with a diameter that ultimately matches or is larger than the graft/tunnel size (e.g., 8 mm graft/tunnel, 8 mm or 1 mm larger in diameter screw). The femoral screw preferably is 8 or 9 mm in diameter, and about 23 mm in length. For interference screw fixation within the tibia, screws are chosen which are 1 mm larger than the size used in the femur. The proximal tibial screw is preferably between about 10-25 mm in length, while the distal tibial screw is about 10-20 mm long overall. Prior to passing the graft, a tunnel notcher (Arthrex Part No. AR-1844) preferably is used to create an anterior-superior starting point for the implant.

Graft 60 is secured in the tibial tunnel 66 bicortically using interference screws 2 and 20, as follows: After the femoral interference screw 40 is installed, proximal tibial screw 2 is guided through tibial tunnel 66 over a guide pin (not shown) and turned or otherwise positioned at the tibial plateau using a cannulated inserter, such as the driver shown in FIGS. 8-10 and described more fully below. The guide pin then is withdrawn, and the distal tibial interference screw 20 is installed to secure the graft at the distal exit 68 of tibial tunnel 66. A distal tibial screw having 1 mm larger diameter than the proximal screw can be used to accommodate any further dilation of the tunnel which may have occurred during prior screw installation. Screw 20 is turned so that the angled face on the back end 26 of the screw implant is substantially flush with the anterior surface of the tibia.

Figure 10:
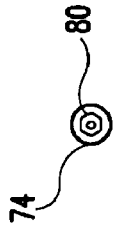
FIG. 10 is a front end view of the driver shown in FIG. 7.
Figure 9:
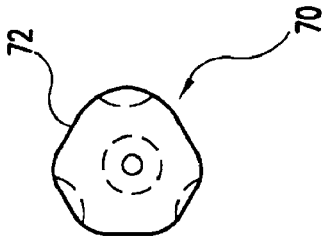
FIG. 9 is a back end view of the driver shown in FIG. 7.
Figure 8:
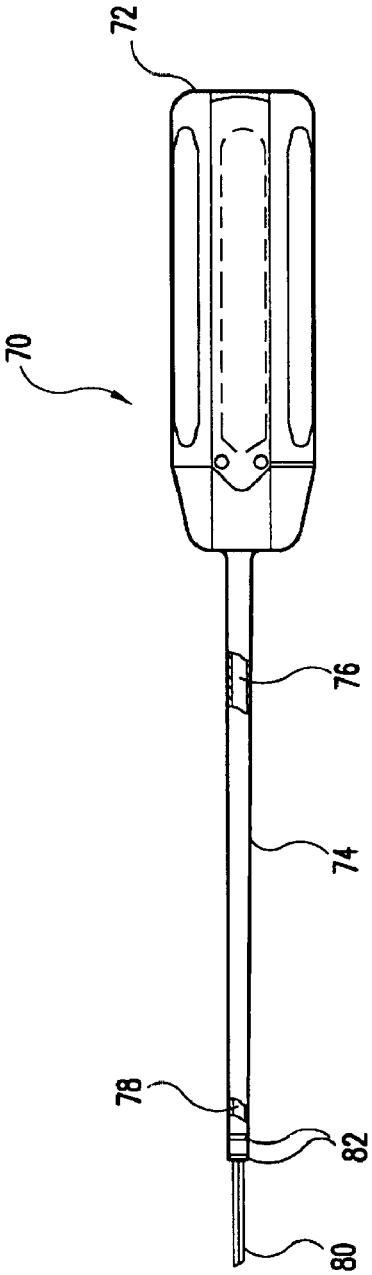
FIG. 8 is an elevation of a driver for a bioabsorbable interference screw according to the present invention.

A preferred driver 70 for a bioabsorbable interference screw will be described with reference to FIGS. 8-10. Driver 70 includes a cannulated handle 72 attached to a cannulated shaft 74. Shaft 74 has a larger diameter cannulated opening 76 in the section closer to handle 72, and a narrower cannulation 78 toward and through drive tip 80. Tip 80 is hexagonal, and has a tapered shape which corresponds to the sockets of bioabsorbable interference screws 2 and 20. Advantageously, the tapered hexagonal drive tip allows for secure engagement of the screws, as described above. Laser depth lines 82 on shaft 74 are provided.

Advantageously, the present invention provides bicortical fixation within the tibial tunnel. The two device method maximizes tibial fixation by securing the soft tissue graft at the cortical bone layers at both the entrance and the exit of the tibial tunnel. The back end of the distal device is angled so that it closely approximates the angle of the distal tibial tunnel rim. The distal device is non-cannulated to prevent hematomas from being formed by blood flowing from the tibial tunnel into the surrounding soft tissue.

The proximal device can be a known device that is positioned up to the tibial plateau to maximize fixation in cortical bone. Preferably, the proximal device has a restricted cannula to minimize the flow of synovial fluid entering the tibial tunnel. The proximal device prevents the graft from moving side to side during cyclic loading, which enhances biological fixation and prevents tunnel widening. Cortical fixation at both ends of the tibial tunnel also advantageously results in the retention of blood between the devices, creating an advantageous environment for healing and incorporation of the graft.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of securing a graft in a *single* bone, the method comprising the steps of:

(*a*) forming a tunnel through the *single* bone, the tunnel having an entrance and an exit at opposing ends of the tunnel;

(*b*) *subsequently to step* (*a*), extending a portion of the graft within the tunnel between the entrance and the exit; and (*c*) *subsequently to step* (*b*), securing the graft within the tunnel to cortical bone *by inserting and rotating interference screws* at both the entrance and the exit of the tunnel to provide bicortical fixation of the portion of the graft in the tunnel.

[2. The method of claim 1, wherein the step of securing the graft comprises installing an interference fixation device at each of the opposing ends of the tunnel.]

3. The method of claim 1, further comprising the steps of extending the graft between the bone and another bone, and securing the graft to the other bone.

[4. The method of claim 1, wherein the step of securing the graft is performed using interference screws.]

5. The method of claim 1, wherein the step of securing the graft is performed using an adhesive.

6. The method of claim 1, wherein the bone is a tibia.

7. The method of claim 1, wherein the graft replaces an anterior cruciate ligament.

8. A set [of fixation devices] for securing [a graft] *an autograft or allograft* in a tunnel formed through a single bone, the tunnel having a proximal end and a distal end located at opposing ends of the tunnel, the set of fixation devices comprising:

*an autograft or allograft;* a proximal [fixation device] *interference screw* configured to secure the [graft] *autograft or allograft* to cortical bone at the proximal end of the tunnel; and a distal [fixation device] *interference screw* configured to secure the [graft] *autograft or allograft* to cortical bone at the distal end of the tunnel, *wherein the distal interference screw is partially cannulated and has a back end with a surface disposed at an angle relative to a central axis of the interference screw*.

9. The set [of fixation devices] of claim 8, wherein the proximal device has a tip with a rounded profile.

10. The set [of fixation devices] of claim 8, wherein the proximal device is fully-threaded.

[11. The set of fixation devices of claim 8, wherein the distal device is partially cannulated and has a back end with a surface disposed at an angle relative to a perpendicular to a central axis of the fixation device.]

[12. The set of fixation devices of claim 8, wherein at least one of the distal device and the proximal device is an interference screw.]

13. The set of [fixation devices according to] claim 8, wherein the proximal and distal [fixation devices] *interference screws* are configured to substantially occlude the respective opposing ends of the tunnel.

[14. An interference screw for graft fixation, the screw having a fully-threaded outer surface, and at least one of a back end with a surface disposed at an angle relative to a perpendicular to a central axis of the interference screw and a front end having a rounded profile.]

*15. A method of securing a graft in a tibia during ligament reconstruction surgery, comprising the steps of:*

*forming a tunnel through the tibia, the tunnel having an entrance at a tibial plateau and an exit at an anterior surface of the tibia;*

*extending a portion of the graft within the tunnel between the entrance and the exit; and*

*securing the graft within the tunnel by inserting, into the exit of the tunnel at the anterior surface of the tibia, an interference screw having a fully-threaded outer surface and a back end with an angled profile and a face disposed non-orthogonally relative to a central axis of the interference screw, the interference screw being turned during insertion so that the angled face of the back end*

*of the screw is substantially flush with the anterior surface of the tibia, to wedge the graft directly against the tibia by the interference screw.*

*16. The method of claim 15, wherein the graft extends between the tibia and a femur, and replaces an anterior cruciate ligament.*

*17. The method of claim 15, wherein the interference screw is formed of a bioabsorbable material.*

*18. The method of claim 17, wherein bioabsorbable material comprises poly-(L-lactic acid).*

* * * * *